(12) United States Patent
Emanuel et al.

(10) Patent No.: US 10,408,809 B1
(45) Date of Patent: Sep. 10, 2019

(54) SAMPLING AND DETECTION KIT FOR CHEMICAL AND BIOLOGICAL MATERIALS

(71) Applicant: U.S. Army Edgewood Chemical and Biological Command, APG, MD (US)

(72) Inventors: Peter A Emanuel, Abingdon, MD (US); Calvin W. Chue, Baltimore, MD (US); Gregory A. Thompson, Baltimore, MD (US); Colin W Graham, Aberdeen, MD (US); Aleksandr E. Miklos, Baldwin, MD (US); Jacob J. Shaffer, Joppa, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 586 days.

(21) Appl. No.: 14/878,266

(22) Filed: Oct. 8, 2015

Related U.S. Application Data

(60) Provisional application No. 62/062,357, filed on Oct. 10, 2014.

(51) Int. Cl.
*G01N 21/00* (2006.01)
*G01N 33/00* (2006.01)
*G01N 21/78* (2006.01)

(52) U.S. Cl.
CPC ....... *G01N 33/0062* (2013.01); *G01N 21/783* (2013.01); *G01N 33/0047* (2013.01); *G01N 2033/0068* (2013.01)

(58) Field of Classification Search
CPC ........... G01N 33/0062; G01N 33/0047; G01N 21/783; G01N 2033/0068
USPC ......................................... 422/85, 83, 82.05
See application file for complete search history.

(56) References Cited

U.S. PATENT DOCUMENTS

2012/0123686 A1\* 5/2012 Xiang .............. G01N 33/48792
702/19
2014/0281479 A1\* 9/2014 Gettings ............ G01N 33/0062
713/150

OTHER PUBLICATIONS

Detection Connection: Partnerships, Innovation help develop Army-specific CB Smartphone detector, Apr. 2014, Edgewood Chemical Biological Center (Year: 2014).\*

\* cited by examiner

*Primary Examiner* — Natalia Levkovich
(74) *Attorney, Agent, or Firm* — Ulysses John Biffoni

(57) ABSTRACT

A device and method for collecting, analyzing, and identifying chemical and biological samples in solid or liquid form is disclosed. The analysis compares the color change of Colorimetric Sensor Arrays (CSAs) over time with images for known materials/compounds contained in a library. The device can be used as a handheld or standalone device and integrates the sampling and detecting functions of the prior art into a single device that analyzes and identifies the sample without destroying it. The inventive volatile organic compound (VOC) technology device is also unique in that it relies on a comparison to a proprietary compound library that is supported by lab data. This compound library identifies the unique dye signature combinations that provide very accurate classification of a wide variety of chemical and biological agents.

9 Claims, 3 Drawing Sheets

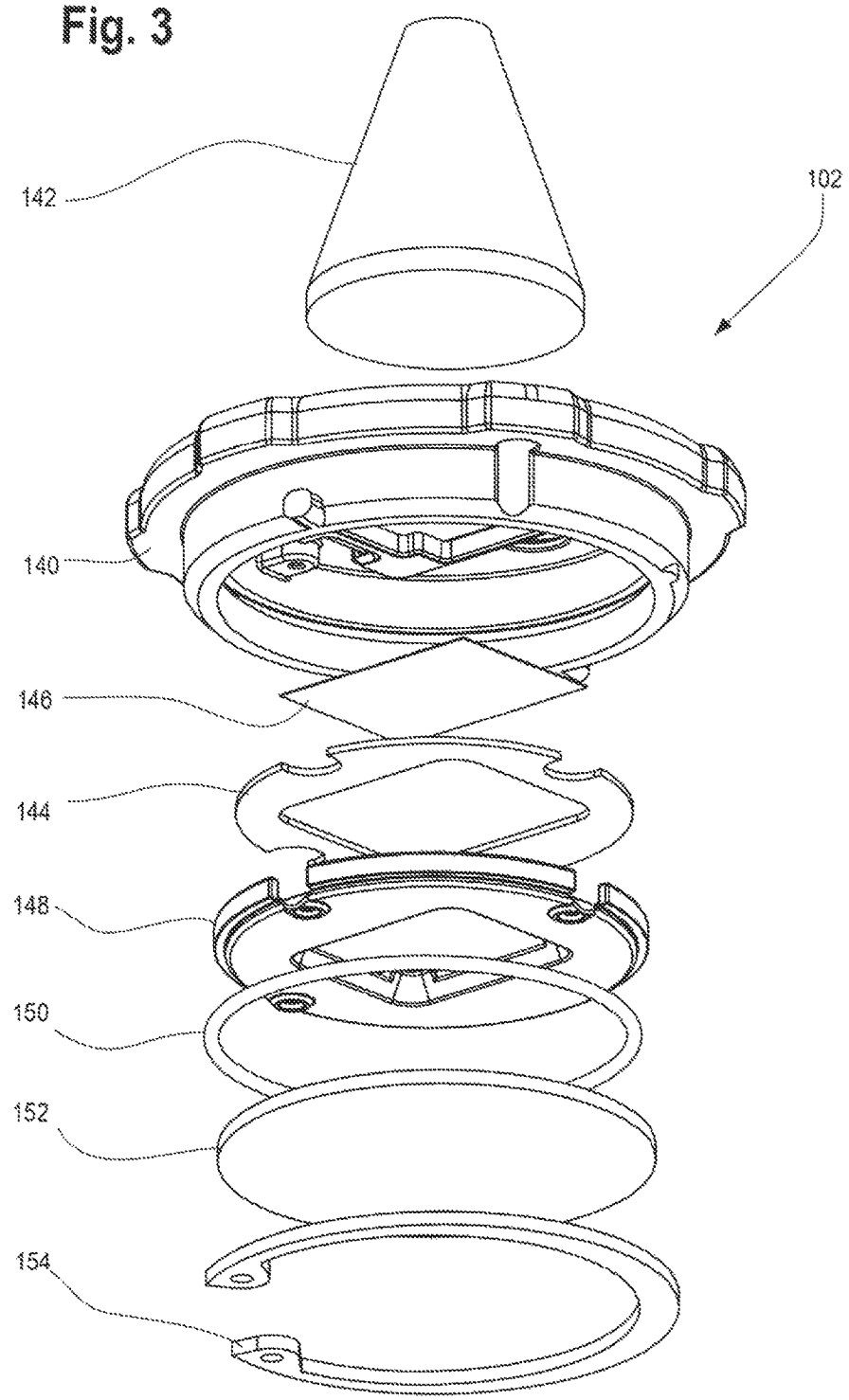

SAMPLING AND DETECTION KIT FOR CHEMICAL AND BIOLOGICAL MATERIALS

PRIORITY

This application claims the benefit of provisional application No. 62/062,357, filed Oct. 10, 2014.

GOVERNMENT INTEREST

The invention described herein may be manufactured, used, and/or licensed by or for the U.S. Government

BACKGROUND

This invention relates generally to a device for collecting and analyzing chemical and biological samples in solid or liquid form. The device can be used as a handheld or stand alone device.

Currently there exist a number of sampling kits that are designed to acquire and safely transport biological specimens or chemical samples. These sampling devices are sometimes packaged or used alongside testing devices that require the sample to be injected into another apparatus for testing. In fact, most prior art sample collection devices that have a sampling component are focused primarily on having that sample taken up and delivering it into a detector.

One example of an environmental sampling kit is the BisKit®. This device is designed to be used in a hazardous environment to collect samples while dressed in protective gear such as the military's mission oriented protective posture (MOPP) gear. The BisKit® is just a sampler and does not provide an analysis of the sample.

Another example of a prior art sampling kit is the Integrated Multiplex Assay and Sampling System—IMASS® from BBI® which collects a biological sample in a liquid form. The sample then wicks into a paper based flow pad and is injected into an antibody based immunoassay. In the IMASS® device the sample is destroyed or altered thus rendering it useless for attribution or forensics.

While many prior art sample collection systems are focused solely on the sample collection, some also provide some analysis of the sample. It is also known to provide information about the sample using colorimetric methods. One example of this type of system is available from 3M® Company and it is called the Clean-Trace® Water ATP kit. This swab based product has integrated protein detection and adenosine triphosphate (ATP) detection. The system was developed for food processing plants to measure generic biological contamination on machinery and metal surfaces. The 3M swab system collects a sample on a cotton swab and then floods the sample with a detection developing reagent that gives off light to detect ATP or changes color to reflect the presence of protein in the sample.

As in the other systems discussed above, the 3M® Clean-Trace® system collects a sample on a swab simply as a means to deliver the specimen to the detection chamber where it is consumed in the analysis. The developing reagent used in the Clean-Trace® system destroys the sample during detection.

There are other volatile organic chemical (VOC) sensing technologies on the market that are used to measure chemicals but few are used on biological samples. One such device is the FOODsniffer which is an electronic 'e-nose' which enables users to determine the quality, freshness of beef, pork, poultry and fish. In theory, four different sensors would pick up data on temperature, humidity, ammonia, and volatile organic compounds, which you would be able to access from an app.

A number of prior art devices measure chemicals using their vapors. These include:

Ion Mobility Spectrometers: Examples of devices that utilize this technology are the Drager® Multi-IMS Chemical Agent Detector, the Environics® USA ChemPro 100i IMS and various portable detection devices from Rae® Systems. A similar technology is flame photometric detectors (AP2C from Proengin® SA and the MINICAMS® from O.I. Analytical® (College Station, Tex.).

Infra-Red (IR) Spectroscopy: Examples of devices that utilize this technology are the M21 Remote Sensing Chemical Agent Alarm (RSCAAL).

Time of Flight Spectroscopy: Measures vapor behavior and to identify using spectroscopic or impedance measurements. An example of this type of device is the T-ION-TVOC Sensor from Ion® Science.

A colorimetric sensing system is also disclosed in U.S. Pat. No. 5,445,795 titled Volatile organic compound sensing devices. The older VOC technology described in this patent relies on a single class of recognition elements that are inorganic double complex salts which change color reversibly when exposed to volatile organic compound (VOC) vapors.

None of the existing technologies for chemical agent detection use disposable paper based arrays of dyes that can be visualized with and imaged by a standard RGB camera. U.S. Army M8/M9 paper has been in use widely for many years but it is not specific and uses a small number of dyes to generically classify materials. It also suffers from many false positives.

Further, none of the existing technologies for chemical agent detection use large collections of sensing dyes or colorimetric dye indicators that collectively contribute to create a unique signature. Further, existing colorimetric systems are focused on explosive detection or chemicals but often rely on heating or the addition of developing reagents (i.e. acids or organics). These techniques add time and complexity to a test. In addition, it is important to note that once a user adds reagents to a sample that sample is permanently altered.

Thus, a need exists for a chemical and biological detection system that is both a sampling device and a detection device. Further, there is a need for a device that uses volatile organic compounds to detect chemical and biological threat materials and doesn't alter, add, or taint the sample.

SUMMARY

The invention relates generally to a device for collecting and analyzing chemical and biological samples in solid or liquid form. The analysis will compare the color change of Colorimetric Sensor Arrays (CSAs) over time and compare the change to a library of CSA images. The device can be used as a handheld or standalone device and integrates the sampling and detecting functions of the prior art into a single device that analyzes the sample without destroying it. The inventive VOC technology device is also unique in that it relies on a comparison to a proprietary compound library that is supported by lab data. This compound library identifies the unique dye signature combinations that classify exactly what the chemical agent is. It does not generically classify the compounds or give a general identification. It is an exact identification.

The invention in one implementation encompasses an analysis device for detecting a volatile organic compound (VOC), including a housing for containing a camera and a processing unit; and a sampling cartridge, said sampling cartridge further including a body, a mechanism for attaching the sampling cartridge to the housing; a sample collection pad inside said body for collecting a sample which generates VOCs; and a colorimetric sensor array (CSA) between the sample collection pad and the housing which reacts to the VOCs on the sample collection pad so that the camera collects images of the CSA for processing by the processing unit to analyze the VOC.

In a further embodiment, the sampling cartridge includes a sampling port in the body opposite of the housing and a removable cap covering the sampling port.

In another embodiment, the housing of the analysis device includes an activation button for activating the camera after a sample is taken.

In an embodiment, the analysis device includes a limit switch that is activated when the sampling cartridge is attached to the housing causing the camera to acquire a preliminary image.

In another embodiment, the analysis device includes a USB port for to connecting a USB drive or cable to allow recharging or powering the device or downloading analysis results and/or a wireless modem for communicating with another computing device.

In a further embodiment, the housing and body are manufactured from material that is impact and slip resistant and the housing and sampling cartridge are sealed and water resistant when attached to each other.

Another embodiment of the invention encompasses a sampling cartridge for use with an apparatus for detecting a volatile organic compound (VOC), the sampling cartridge including a body having a sampling port; a removable cap attached to a first side of the body and covering the sampling port; a sample collection pad inside said body and adjacent to the sampling port; a colorimetric sensor array (CSA) inside said body and adjacent to the sample collection pad on the opposite side from the sampling port; a lens adjacent to the CSA, said lens attached to a second side of said body so as to seal the sample collection pad and CSA inside the body; and a mechanism for attaching the second side of the body to the apparatus for detecting a VOC.

In a further embodiment, the mechanism for attaching the sampling cartridge includes a plurality of tabs that interlock with corresponding notches the apparatus for detecting.

In yet another embodiment, chemical or biological samples in solid or liquid form or liquid form can be collected using the sampling cartridge.

In a further embodiment, the sample collection pad is a synthetic polyurethane foam pad, polyethylene terephthalate (PETE) fiber material or a trypticase soy agar (TSA) surface for collecting biological samples that may grow upon the surface collection material.

Another implementation of the invention encompasses a method of collecting and analyzing samples using a sampling cartridge with a reusable imaging dock, including the steps of attaching a sampling cartridge to the reusable imaging dock; taking an preliminary image of the sampling cartridge; acquiring a chemical or biological sample using the sampling cartridge; pressing an activation button; taking a first image of the sample in the sampling cartridge; taking additional images of the sample in the sampling cartridge at a series of intervals; and analyzing the sample using the images.

In another embodiment, the sample reacts with color changing dyes on a colorimetric sensor array (CSA) in the sampling cartridge and the images of the sample are images of the CSA.

In a further embodiment, images of a CSA are analyzed by comparing them to a library of images of CSAs reacting to known compounds.

In another embodiment, different sampling cartridges are used to collect chemical and biological samples.

In yet a further embodiment, images of samples and analysis results are downloaded from the reusable imaging dock by means of a USB port or a wireless connection.

In another embodiment, the method includes the steps of controlling the analysis of an image by setting at least an test event start time, an exposure time, image transfer, light levels, image sensor calibration, target test type, LED alerts, or device wireless connectivity.

In yet another embodiment, the method includes the step of connecting the reusable imaging dock to another computing device using a wireless or wired connection.

DESCRIPTION OF THE DRAWINGS

Features of example implementations of the invention will become apparent from the description, the claims, and the accompanying drawings in which:

FIG. 3 depicts an exploded view of a cartridge for use with the device of FIG. 1.

DETAILED DESCRIPTION

If used and unless otherwise stated, the terms "upper," "lower," "front," "back," "over," "under," and similar such terms are not to be construed as limiting the invention to a particular orientation. Instead, these terms are used only on a relative basis.

According to an embodiment, the invention provides a self-contained sampling and detection device for chemical and biological materials. The device provides the user with a quick way to collect samples as well as transport them. In addition, the device makes use of the time spent transporting the sample back to a higher fidelity analytical laboratory to analyze the sample. Specifically, the device is analyzing the volatile organic compounds in the sample during transport.

Overview

Figure 1:
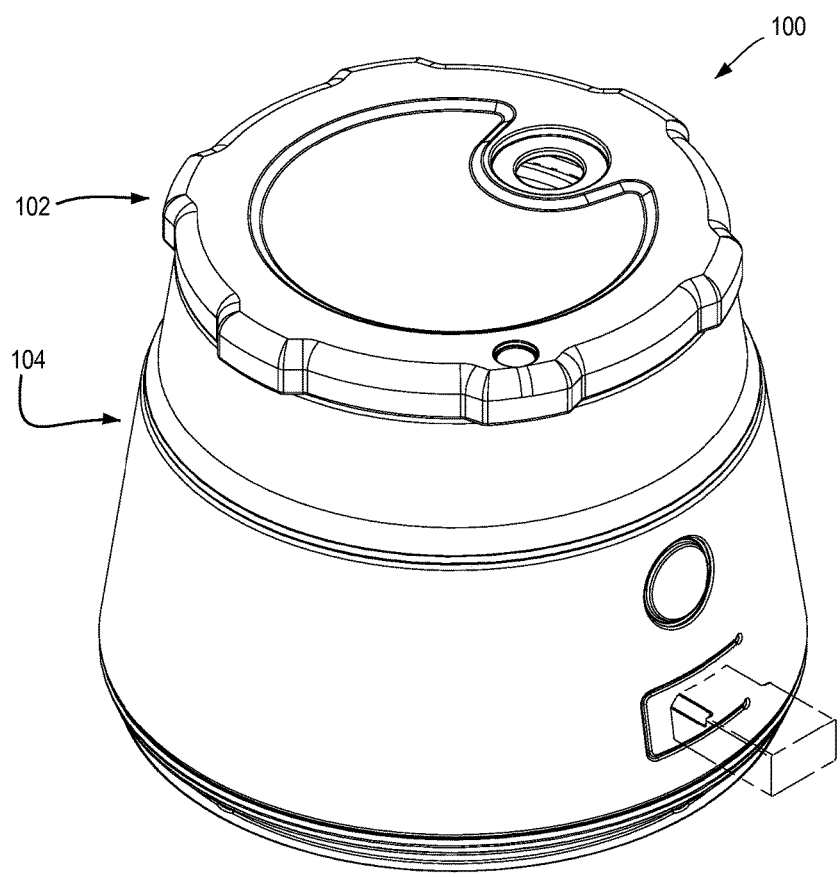
FIG. 1 depicts a VOC sampling and detection device according to the present invention.

A VOCkit device 100 according to the invention is shown in FIG. 1. Disposable cartridge 102 is attached to a reusable imaging dock 104. This allows successive cartridges to be attached to dock 104, or cartridges 102 having different shapes and sampling capabilities to be used with a single imaging dock 104.

In an embodiment, VOCkit device 100 may be manufactured out of materials that are impact resistant to prevent contamination of the sample and sealed to prevent contamination and to protect sensitive electronics. In an embodiment, device 100 is water resistant at a minimum when all components are in place. In a further embodiment, housing 106 is covered with a slip resistant surface, for example, rubber or textured material, to facilitate handling by a user who may be wearing gloves or other protective gear. The imaging dock is constructed so that it may be wiped-down for decontamination.

In a further embodiment, VOCkit device 100 may be manufactured out of materials that are chemically resistant and that will not interact or interfere with the volatile organic compounds signature of the collected sample, thus ensuring accurate analysis.

Figure 2:
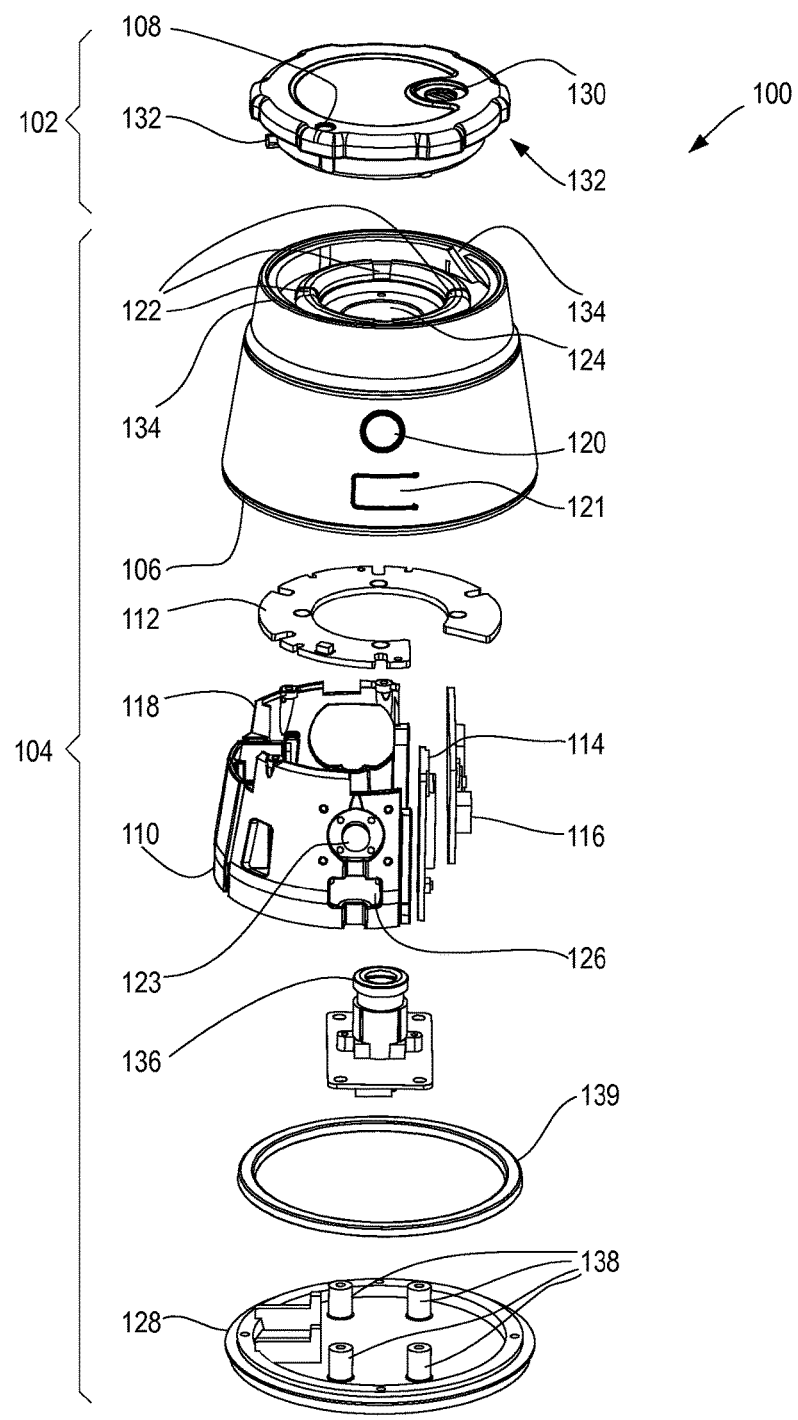
FIG. 2 depicts an exploded view of the device of FIG. 1.

An exploded view of VOCkit device 100 is shown in FIG. 2. Cartridge 102 includes an LED indicator light 108 which indicates that cartridge 102 is securely attached to dock 104. Cartridge 102 also includes a sampling port 130, as explained in connection with FIG. 3.

Main housing 106 contains and protects the components of dock 104. Tabs 132 and notches 134 assist in positioning and attaching cartridge 102 to housing 106. In an embodiment, there are two tabs and corresponding notches on opposite sides of cartridge 102 and housing 106 but any number and location of tabs and notches could be used to provide a secure attachment.

Inside the upper portion of main housing 106, a compartment adjacent to cartridge 102 includes a plurality of LEDs 122 for illuminating a sample in cartridge 102. Lens 124 provides a window between this compartment and electronics within housing 106. A button 120 is used to begin operation of reusable imaging dock 104 as explained in more detail below. A USB port 121 is provided to enable the connection of a USB drive or cable to allow recharging/powering the device or downloading analysis results.

An electronics cradle 110 is contained within housing 106. Cradle 110 holds the various components used to analyze a sample in cartridge 102. LED circuit board 112 controls LEDs 122. Additional components include processing unit 114, wireless modem 116, rechargeable battery 118, power/data connector 126 and inner button 123 which is activated when button 120 is pressed. A limit switch (not shown) in electronics cradle 110 is depressed when a cartridge is attached to housing 106. In an embodiment, one or more LED indicators (not shown) are provided to alert the user to device status. These indicators may also be deactivated for more discrete operation.

Camera 136 is mounted to base cover 128 using mounting attachments 138. Camera 136 is used when analyzing a sample, as explained in further detail below. A secure seal between base cover 128 and housing 106 is maintained by O ring 139.

Processing unit 114 will analyze images of a sample in cartridge 102 taken by camera 136 over time, and then determine the composition of the sample collected. The device will use LED illumination from LEDs 122 of FIG. 1 to light the sample for accurate and consistent color representation as described below. Housing 106 and cartridge body 140 may be opaque in order to stop external light from impacting color recognition by the camera as well as to prevent radiating light outside of the device.

Sampling Cartridge

Sample collection using device 100 is accomplished with disposable sample collection cartridges 102 as shown in an exploded view in FIG. 3. Cartridge body 140 includes sampling port 130 (visible in FIG. 1) which is covered by sealing cap 142. Although a specific form is shown for sealing cap 142, any shape or configuration of sealing cap could be used. Sample collection pad 144 is made from absorbent material and located immediately inside body 140 so as to receive samples through sampling port 130. A Colorimetric Sensor Array (CSA) 146 is used in analyzing a collected sample. CSA 146 is held in place by CSA retainer 148. An O ring 150 provides a seal between CSA retainer 148 and lens 152 so that samples are sealed inside cartridge 102. Snap ring 154 is used to secure the interior components inside cartridge body 140.

Sample collection pad 144 of the device has been designed to vary depending on what is being sampled. In some embodiments it is a synthetic polyurethane foam pad, or polyethylene terephthalate (PETE) fiber material. As an alternative, for example in other biological sampling situations, it will be a high concentration trypticase soy agar (TSA) surface that will harbor a biological sample that may grow upon the surface collection material during transport. Sampling can be done on a multitude of surfaces including but not limited to concrete, vinyl, wood, glass, and nylon. Collection of both wet and dry samples is possible.

CSA 146 features a piece of paper or other absorbent material, also referred to as a ticket, which has been impregnated with a plurality of discrete dye dots. Each dye dot reacts with different chemical and biological compounds on collection pad 144 by changing color. In an embodiment, a 10 by 10 grid of unique dye spots is used for CSA 146 but any preferred number or arrangement may be used. Examples of dye spots which may be used for the CSA 146 are described in detail in U.S. Pat. Nos. 6,368,558; 6,495,102; 7,261,857, and 8,852,504, all of which are incorporated by reference in their entirety herein.

The ticket is imaged by camera 136. The image format is standard RBG format with adequate pixels to accurately define each discrete dot. In an embodiment, this is defined as a minimum of 480×600 pixels however any appropriate number of pixels may be used. The camera operation is controlled by the processing unit 114 which also stores recorded images for future analysis. Images are recorded at intervals received from a computing device and set by the user as explained below.

Sampling cartridge 102 includes a small chamber that allows for the sampled substance to evolve volatile organic compounds which collect within the chamber. CSA 146 is located within that headspace which allows the VOC substances to interact with CSA 146 to affect change. In an alternative embodiment, cartridge 102 allows for collection of liquid samples that wet collection pad 144 and wick into the CSA 146. Vapor or liquid contact will affect the dye collections of CSA 146 to elicit a unique response that identifies the compounds of interest.

Operation

Before device 100 is ready for use, a calibration operation is performed. This is done using color standards to mitigate possible manufacturing differences between same generation devices as well as different versions of device 100.

The calibration operation involves normalizing the orientation of the image. The application takes each photo and rotates it to a standard angle. This is done by locating black dots on the CSA array 146. These dots are produced in specific locations. Once located, each dot's current location is used to calculate the current angle of the array and rotate it appropriately during image processing.

To take a sample using VOCkit device 100, sampling cartridge 102 is locked into place onto main housing 106 of the reusable imaging dock 104 using tabs 132 and notches 134.

Installing the cartridge depresses the limit switch (not shown) which causes camera 136 to take a reading of sampling cartridge 102 at time "0" for use in subsequent analysis. At this time, VOCkit device 100 is ready for use in subsequent sampling and analysis functions.

When a user is prepared to take a sample, the user removes cap 142 from sampling cartridge 102 to expose collection pad 144. The user presses collection pad 144 against the area to be sampled in order to capture the liquid or powder sample on collection pad 144 and then replaces cap 142 on body 140. In alternative embodiments, collection pad 144 may absorb vapors from a sample or an eye dropper may be used to introduce a liquid sample to collection pad 144 through sampling port 130. Once cap 142 is replaced on the cartridge, cartridge 102 is leak proof and can be stored or transported in any orientation. Cartridge 102, cap 142, and imaging dock 104 are all designed in a way to protect the sample from contamination as well as to contain the sample. Once the sample has been acquired, the user depresses the side button 120 to activate the imaging systems within main housing 106 of reusable imaging dock 104. Activating VOCkit device 100 will automatically trigger camera 136 to take a picture, or baseline image, of CSA 146 located inside sampling cartridge 102.

This baseline image will be used for comparison with subsequent images taken automatically at programmed intervals. These image intervals will vary depending on whether a biological (1 hour intervals) or chemical (15 minute intervals) sampling cartridge is being used. The sealed VOCkit device 100 containing the sample can now be set aside or prepared for transport. It will take images at pre-set intervals that will locate, distinguish, and image every dye spot in CSA 146. Each spot is assigned numerical values of red, green, and blue (RGB). These RGB values will be subtracted from the starting RGB values for that specific dye to give a differential map across time. The collective differential maps for the complete selection of dyes will result in a unique signature of volatile organic compounds. Device 100 will compare the signatures against a proprietary compound library in the form of a database of known compounds to identify compounds of interest within the sample. The proprietary compound library is developed from and supported by lab data as explained in more detail below.

The next step in analyzing an image is quantifying the image. The software first locates all available dots on the ticket. The software then takes each dot and determines its color value. This is done for the both the unexposed ticket and the exposed ticket. Once these values are determined the software computes the difference values between the unexposed and exposed ticket. These values make up the signature of the tested compound.

The final step is the detection step. The software uses a k-nearest neighbor algorithm to determine if a signature of the tested compound matches any signatures within the signature library of the software. The library is both pre-defined and customizable. If a compound is not currently in the library, the user can custom program signatures using known samples. This signature is then available to other users once verified by the software developer.

A computing device coupled to VOCkit device 100 contains an application developed to operate on mobile devices including smartphones, tablets, and other computing devices. The application has two primary functions. It determines if VOCkit device 100 has detected a known compound and it controls multiple aspects of the VOCkit device.

Through a Graphical User Interface (GUI) of the application, a user is able to remotely control at least the following aspects of the device: test event start time, exposure time, image transfer, light levels, image sensor calibration, target test type, LED alerts, and device wireless connectivity. The GUI displays device information including battery levels, wireless signal strength, and test status and allows a user to view images to verify device operation for diagnostics and system checks. The GUI allows transmittal of results to remote users given the computing device has a communication connection available for the software to utilize. In addition, the application contains a chemical and biological compound signature library. This library is made up of difference image values. These values are the color shift values between exposed and unexposed CSA arrays 146. The application does comparative analysis on CSA array 146 to determine if its signature matches one in the software's library. This comparative analysis involves comparing the unexposed CSA ticket (as determined by depressing limit switch 108 at time "0") to the exposed CSA ticket after a period or multiple periods of time.

In an embodiment, the user will be able to select agents that he/she wishes to be alerted about should they be identified. For example, a user may wish to be alerted to the presence of traditional chemical nerve agents or toxic industrial chemicals. These customized search and alert menus will be modified prior to beginning the sampling operation. Once device 100 has located a specific signature of an agent of concern it will send a signal via a wireless method, for example, Bluetooth (unsecure, low cost and short distance) or Ultra Wideband (secure with higher cost), to a computing device that has been synced with VOCkit 100. A wired method could also be used to transmit information if a wireless connection is not available or desirable. It will transmit a presumptive identification to an application that is loaded on to the computing device. In this way the sampling kit has non-destructively tested the sample during the time used to transport it to another location and communicated those findings to a second device.

VOCkit device 100 provides a number of advantages over the prior art. It is the first sampler that can be both a chemical sampler and detector or a biological sampler and detector. By employing interchangeable sampling cartridges on a reusable docking and detection platform a user can take both types of samples. Device 100 is adapted to work in a hazardous chemical or biologically contaminated environment and to be easily manipulated while in MOPP gear.

An additional feature of the inventive device 100 is that it is reliant on a signature database developed by the US Army Edgewood Chemical Biological Center in which the VOC dye arrays have been tested against hundreds of chemical and biological samples. This signature database allows the discrimination of traditional and non-traditional chemicals agents, toxic industrial chemicals (TICS), toxic industrial materials (TIMS) and biological pathogens. VOCkit device 100 passively reacts to vapors that evolve in the sensing chamber and does not require addition of other reagents, whether liquids or gases. That means that the sample is not consumed by the test and is available for further testing once the sample chamber is opened. In addition, the proprietary compound library is based around the same materials used to manufacture device 100 so as to take into account any possible interference. The signature database can reside in the Smartphone or tablet as part of the application or, if preferred, it can reside within processor unit 114 of VOCkit 100 itself.

VOCkit device 100 relies on up to 100 different colorimetric dyes that each react in different ways to different classes of chemicals and VOC vapors. It is not a single dye or class of reagent that makes up the VOC paper sensing array. There are many different classes of dye indicators represented. The cumulative collection of these many dyes allows for versatility and detection across a broad spectrum of VOC vapors. The varying VOC array responses are interpreted by a camera that compares the response against a signature database. Unlike other colorimetric systems previously described there is no single class of dye in this device that dominates in this discrimination but rather the contribution of many dye types. This combination of responses is the basis for the unique signature database.

VOCkit device 100 offers the advantage that, unlike other sampling devices, the device incorporates a reusable electronic reader and imager. This reusable base transmits an archived copy (JPEG, TIFF) of analysis results to provide real time presumptive identification. It also provides a geo-tagged location for where the suspect sample originated. The transmission of VOCkit data occurs by syncing with computing devices (i.e. Smartphones, tablets, or computers) that are loaded with a compatible application program as described above.

Numerous alternatives to the invention exist. Any type of substance may be tested using the device of the invention. Although the device is disclosed as being directly manipulated by a user, it is possible to drop or insert the device into an area so that a sample may be taken remotely.

VOCkit device 100 in one example comprises a plurality of components such as one or more of electronic components, hardware components, and computer software components. A number of such components can be combined or divided in the apparatus 100. Processing unit 114 of device 100 employs and/or comprises a set and/or series of computer instructions written in or implemented with any of a number of programming languages, as will be appreciated by those skilled in the art.

The steps or operations described herein are just for example. There may be many variations to these steps or operations without departing from the spirit of the invention. For instance, the steps may be performed in a differing order, or steps may be added, deleted, or modified.

Although example implementations of the invention have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An analysis device for detecting one or more volatile organic compounds (VOCs), comprising:
    a housing, said housing including a camera and a processing unit, said processing unit operatively connected to said camera to control operation of the camera; and
    a sampling cartridge, said sampling cartridge comprising:
        a body;
        a mechanism for attaching the sampling cartridge to the housing;
        a sample collection pad inside said body for collecting a sample which generates VOCs; and
        a colorimetric sensor array (CSA) between the sample collection pad and the housing, wherein said CSA includes a plurality of dye dots and each of said dye dots includes a different colorimetric dye configured to react with different VOCs on the sample collection pad with a change in color; and
    wherein the camera collects images of the CSA for processing by the processing unit to analyze and identify the VOC based on the color changes of the dye dots, and wherein said processing unit is configured for comparing the images from the CSA to a library of images of CSAs reacting to known compounds, wherein the comparison is based on a baseline image being used for comparison with subsequent images taken automatically at programmed intervals.

2. The analysis device of claim 1, wherein the sampling cartridge further includes a sampling port in the body opposite the housing, and wherein said sampling port provides direct access to said sample collection pad for depositing a sample on said sample collection pad.

3. The analysis device of claim 2, wherein the sampling cartridge further includes a removable cap covering the sampling port.

4. The analysis device of claim 1, wherein the housing further includes an activation button operatively connected to the camera for activating the camera after a sample is taken.

5. The analysis device of claim 1, wherein the housing further includes a USB port for connecting a USB drive or cable to allow recharging or powering the device or downloading analysis results.

6. The analysis device of claim 1, wherein the housing includes an upper portion adjacent the cartridge, said upper portion including a plurality of LEDs for illuminating a sample in the cartridge.

7. The analysis device of claim 6, wherein the upper portion includes a lens providing a window between the upper portion of the housing and the camera.

8. The analysis device of claim 1, wherein the housing further includes a wireless modem for communicating with a computing device external to said analysis device.

9. The analysis device of claim 1, wherein the housing and body are manufactured from rubber or textured material that is impact and slip resistant.

* * * * *